United States Patent [19]

O'Sullivan

[11] Patent Number: 4,544,656

[45] Date of Patent: * Oct. 1, 1985

[54] PHARMACEUTICAL COMPOSITION AND METHOD OF TREATING PSORIASIS

[76] Inventor: Donncha O'Sullivan, 6 Greenfield Crescent, Donnybrook, Dublin 4, Ireland

[*] Notice: The portion of the term of this patent subsequent to Sep. 25, 2001 has been disclaimed.

[21] Appl. No.: 497,207

[22] Filed: May 23, 1983

[30] Foreign Application Priority Data

Aug. 17, 1982 [IE] Ireland .................................. 1981/82

[51] Int. Cl.$^4$ .......................................... A61K 31/185
[52] U.S. Cl. ..................................... 514/228; 514/255; 514/578; 514/665
[58] Field of Search ...................... 424/303, 248.5, 250

[56] References Cited

U.S. PATENT DOCUMENTS

| 3,873,467 | 3/1975 | Hunt | 424/3 X |
| 4,133,717 | 1/1979 | Johnson et al. | 435/253 |
| 4,246,194 | 1/1981 | Ferguson | 424/315 X |
| 4,251,387 | 2/1981 | Lim et al. | 424/32 X |
| 4,473,569 | 9/1984 | O'Sullivan | 424/248.5 |

OTHER PUBLICATIONS

Good et al., Biochemistry, vol. 5, pp. 467–477, 1966.

Primary Examiner—Leonard Schenkman
Attorney, Agent, or Firm—Birch, Stewart, Kolasch & Birch

[57] ABSTRACT

A method of treating psoriasis and similar or related ailments comprises applying to an affected skin area a therapeutically effective amount of at least one skin-compatible zwitterionic aminosulfonic acid (ZASA) of the formula $$RNR'SO_3H$$

wherein R is a straight or branched chain aliphatic radical, or RN is a substituted or unsubstituted nitrogen-containing heterocycle which may have one additional hetero atom; and R' is $C_{2-4}$ straight or branched chain alkylene radical. A pharmaceutical composition is also provided, and comprises at least one ZASA of the above formula together with a pharmaceutically acceptable topical carrier or base.

18 Claims, No Drawings

PHARMACEUTICAL COMPOSITION AND METHOD OF TREATING PSORIASIS

FIELD OF THE INVENTION

This invention relates to a method of treating psoriasis, and to pharmaceutical compositions useful in such treatment.

Psoriasis is a group of disfiguring and uncomfortable skin conditions for which physicians have long sought effective treatment methods. Its causes and etiology are very imperfectly understood. The term "psoriasis" as used in this specification designates not only the known five or six conditions commonly so designated in medical practice, but also, for the sake of simplicity in terminology, other related skin disorders namely the ichtyoses group, the dyskeratoses group and Dariers disease.

BRIEF DESCRIPTION OF THE PRIOR ART

The principal known compositions which have been used with greater or lesser success in the treatment of psoriasis belong to two groups: (1) coal tar products, (2) cortisone products. Group (1) compositions are variable and unpredictable in their effects, but their overall success in symptom alleviation has been small. Some of them cause undesirable skin discoloration. Group (2) compositions bring striking short-term benefit to sufferers, but are attended by well known undesirable side-effects which constitute a contraindication of extended periods of treatment.

BRIEF SUMMARY OF THE INVENTION

It is an object of the invention to provide a method of treatment and pharmaceutical compositions, which will contribute to supplying the medical need mentioned above.

The invention accordingly provides a method of treating psoriasis which comprises applying to an affected area of skin a therapeutically effective amount of at least one skin-compatible zwitterionic aminosulfonic acid (hereinafter ZASA) having the formula

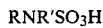

$$RNR'SO_3H$$

wherein either R is a $C_{1-6}$ straight or branched chain aliphatic radical *or* the combination RN is a substituted or unsubstituted nitrogen-containing heterocyclic radical which may have one hetero-atom additional to the nitrogen atom that links said radical to R'; and R' is a $C_{2-4}$ straight or branched chain alkylene radical.

Preferably the ZASA has at least one $pK_a$ value at 20° C. in the range 6.0–8.3 to permit its use on human skin (i.e. the molecule exists mainly in its dipolar form in the pH range 6.0–8.3). All $pK_a$ values qouted in this specification are at 20° C.

Preferred heterocyclic values for RN are N-piperazinyl, N-morpholinyl and N-[N'-(2-hydroxyethyl)]-piperazinyl.

A preferred aliphatic value for R is tris-(hydroxymethyl)-methyl.

Preferred values for R' are —CH$_2$—CH$_2$— and —CH$_2$—CH$_2$—CH$_2$—.

Preferred ZASA's are:

2-(N-Morpholinyl)-ethane sulfonic acid (hereinafter MES) which has a $pK_a$ of 6.15;

2-[N-[N'-(2-Hydroxyethyl)]-piperazinyl]-ethane sulfonic acid (hereinafter HEPES) which has a $pK_a$ of 7.55;

3-[N-[N'-(2-Hydroxyethyl)]-piperazinyl]-propane sulfonic acid (hereinafter HEPPS);

2-[N-[tris-(Hydroxymethyl)]-methylamino]-ethane sulfonic acid;

2-(N-Piperazinyl)-ethane sulfonic acid;

2-(N-Piperazinyl)-propane sulfonic acid;

Piperazine-1,4-bis(2-ethane sulfonic acid) (hereinafter PIPES) which has a $pK_a$ of 6.8; and N,N-bis-(2-Hydroxyethyl)-2-aminoethane sulfonic acid (hereinafter BES) which has a $pK_a$ of 7.15.

The ZASA's mentioned above are known in the chemical literature as buffers. Most of them are described among other compounds by Good, N. et al., in Biochemistry 1966, 5, 467. Preferred ZASA's are mild and cause no skin irritation.

The invention also provides a pharmaceutical composition for application to the human skin in the treatment of psoriasis comprising at least one of the above ZASA's as active ingredient, together with a pharmaceutically acceptable topical carrier or base.

The effective proportion of the active ingredient, by weight of the composition, is in the range 0.05 to 20%, preferably 0.05 to 5%. In the most preferred compositions the effective proportion lies in the range 0.1% to 1.0%.

Not every compound falling within the general definition given above is preferred or suitable for use in the method or composition of the invention. Some few of them are contraindicated or unsuitable for one reason or another.

Reasons for unsuitability, and thus for exclusion from the present invention, include incompatibility with the chosen topical base. Substances forbidden by health or hygiene regulations are prima facie unsuitable and excluded. Known carcinogens, or substances suspected on reasonable grounds of being carcinogens, are excluded. Substances which have any deleterious effect on the skin are excluded. Some of the compounds, for example, cause irritation, reddening or chapping of the skin when used over a short period, or a long period, and are excluded. Others are excluded because they can dye or pigment the skin. These reservations do not, of course, apply to any of the preferred compounds.

Nevertheless the exclusion of unsuitable compounds is a matter well within the competence of a person skilled in the art. Carcinogens, for example, can be identified by consulting published lists of such substances. Incompatibility with the chosen topical base is an empirical matter, to be determined by stability tests. Health and hygiene regulations can be presumed known to persons skilled in pharmaceutical formulation. Any candidate compound can be tested on labelled small areas of healthy skin for undesirable effects such as skin irritation, reddening, chapping, dyeing and pigmenting. The number of unsuitable compounds, as a fraction of the number of ZASA's embraced by the above description, is very small.

The topical base is selected from a wide variety of compositions formulated according to known principles for pharmaceutical purposes. Such compositions include creams, solids, ointments, lotions and film-forming solutions among others. They may be presented in boxes, jars or squeezable tubes, both collapsible and non-collapsible. The solids may be presented as sticks for rubbing on to the skin. Some of the topical bases may be presented as papers, woven or non-woven fabric pieces, or pads, all impregnated with the composition.

DETAILED DESCRIPTION OF THE INVENTION

The invention will be appreciated in greater detail from the following examples of specific embodiments thereof.

EXAMPLE 1

A vanishing cream is made up from the following recipe:

|  | PARTS BY WEIGHT |
|---|---|
| A. OIL PHASE | |
| Stearic acid | 13.0 |
| Microcrystalline wax | 6.5 |
| Olive oil | 3.5 |
| Glyceryl monostearate (acid-stable grade) | 3.5 |
| Polyoxyethylene sorbitan monolaurate[1] | 12.0 |
| Silicone fluid (200-350 centistokes) | 3.0 |
| B. AQUEOUS PHASE | |
| HEPES | 0.2 |
| Water (q.s. ad 100.0) | 58.3 |

[1]The product sold under the trade name TWEEN 20.

The ingredients of A are melted together and brought to 80° C. The ingredients of B are made into a solution, brought to 80° C., and added at that temperature to the melt, with mixing, which is then continued until the emulsified mass has cooled to 40° C. The product is suitably packed so as to prevent evaporation, since it is an oil-in-water emulsion.

This cream is applied to an area of skin showing psoriatic symptoms, preferably several hours before the skin is due to be washed. The application may be repeated after washing.

EXAMPLE 2

An application stick is made from the following ingredients:

|  | PARTS BY WEIGHT |
|---|---|
| Eutanol G[1] | 39.0 |
| Comperlan HS[1] | 11.0 |
| Stearic acid | 10.0 |
| HEPPS | 5.0 |
| Ethanol 96% v/v | 20.0 |
| Glycerol | 15.0 |

[1]Henkel International, Federal Republic of Germany.

The ingredients other than ethanol are mixed and melted together. The temperature of the melt is brought below 70° C., whereupon the ethanol is added and well mixed in. The melt is poured into suitable moulds and allowed to set. The resulting moulded sticks are removed from the moulds, wrapped individually in aluminium foil and packed.

A stick is rubbed gently on to an area of skin showing psoriatic symptoms. These sticks may conveniently be carried in a patient's pocket or handbag.

EXAMPLE 3

An ointment is made from the following ingredients:

|  | PARTS BY WEIGHT |
|---|---|
| Liquid paraffin | 11.0 |
| Petroleum jelly | 30.0 |
| Paraffin wax | 6.0 |
| Glycerol | 38.0 |
| Polyoxyethylene homogeniser | 10.0 |
| HEPPS | 5.0 |

The ingredients other than glycerol are melted together. The temperature of the melt is brought below 70° C. whereupon the glycerol is added with good stirring. The ointment is cooled to room temperature with further agitation, and when cool is passed once through a conventional ointment mill. This ointment is suitable for treating larger areas of skin, or where the cosmetic effect of treatment is deemed unimportant.

EXAMPLES 4 AND 5

These are creams of the vanishing type. They are made up from the following sets of ingredients:

|  | PARTS BY WEIGHT | |
|---|---|---|
|  | Example 4 | Example 5 |
| A. OIL PHASE | | |
| Stearic acid | 10.0 | 10.0 |
| Beeswax | 2.0 | 2.0 |
| Paraffin wax | 12.0 | 10.9 |
| Polyoxyethylene sorbitan monolaurate[1] | 10.9 | 10.0 |
| Glycerol monostearate (acid stable grade) | 5.0 | 5.0 |
| D.C. Silicone fluid 200/350 (Dimethyl siloxane) | — | 2.5 |
| B. AQUEOUS PHASE | | |
| HEPES | 1.0 | 1.0 |
| Sorbitol | 10.0 | — |
| Magnesium sulphate | 0.1 | 0.1 |
| Water (q.s. ad 100) | 49.0 | 58.5 |
| TOTAL | 100.0 | 100.0 |

[1]Commercially available under the trade name TWEEN 20.

The ingredients of B are made into a solution, brought to 90° C.-95° C., and added with stirring to the melted and mixed ingredients of A at about 80° C. Stirring is continued until the temperature falls below 35° C. or until the cream has set.

These creams are packed and used as described in Example 1.

EXAMPLES 6 AND 7

These vanishing creams contain as active ingredients at least one of the biological buffers described by Good, N. et al., Biochemistry 1966, 5, 467. Of the zwitterionic buffer substances therein described, the ones here used have been found particularly suitable. Their names, as previously indicated, are herein abbreviated for convenience to MES and PIPES. The creams are made up from the following ingredients:

|  | PARTS BY WEIGHT | |
|---|---|---|
|  | Example 6 | Example 7 |
| A. OIL PHASE | | |
| Stearic acid | 10.5 | 10.5 |
| Sunflower oil | 3.5 | 3.5 |
| Silicone fluid | 4.0 | 4.0 |
| Glycerol monostearate | 5.0 | 5.0 |
| Paraffin soft white | 2.0 | 2.0 |
| Tween 20 (see Ex. 8-9) | 10.0 | 10.0 |

-continued

| | PARTS BY WEIGHT | |
|---|---|---|
| | Example 6 | Example 7 |
| B. AQUEOUS PHASE | | |
| MES | 4.0 | — |
| PIPES | — | 0.1 |
| Water (q.s. ad 100) | 61.0 | 64.9 |
| TOTAL | 100.0 | 100.0 |

The B ingredients are made into a solution and brought to 90° C.–92° C., then added with stirring to a melt of the A ingredients made at 95° C.–100° C. and cooled to 90° C. Stirring is continued until the cream has set (below 35° C.).

The creams are packed and used as described in Example 1. They can be removed from the hands by a simple soap and water wash, like the products of all the examples.

EXAMPLE 8

This example illustrates a typical formulation which can be used for the pharmaceutical presentation of any of the zwitterionic substances (ZASA's) the newly discovered medical properties of which are disclosed in the present specification.

| INGREDIENT | PARTS BY WEIGHT |
|---|---|
| Stearic acid | 10.0 |
| Vegetable oil (e.g. Sunflower) | 9.0 |
| Glyceryl monostearate (self-emulsifying) | 2.5 |
| Silicone oil (200–350 centistokes) | 0.5 |
| TWEEN 20 (Polyoxyethylene sorbitan monolaurate) | 8.0 |
| The selected ZASA | 0.1 to 1.0 |
| Water (q.s. ad 100) | 69.9 to 69.0 |

The ingredients are put together by known pharmaceutical procedures, such as those set out in the previous examples.

In addition to preservatives, other conventional pharmaceutically acceptable additives may be incorporated in the compositions of the invention. These include, for example, humectants, film formers and water repellents. Sorbitol is a useful humectant. A 4% mucilage of Methyl cellulose is a useful film former. The dimethyl silicones sold by Imperial Chemical Industries Ltd., of the U.K. under the trade designations F 110 and F 111, are useful water repellents.

The ZASA's herein prescribed, when used in proportions in the range 0.1 to 1.0% by weight of a pharmaceutical composition of the invention, are mild and cause no skin irritation. When applied regularly over a period of weeks to clean dry skin initially showing psoriatic symptoms, they have been shown firstly to ease the cracked, dry skin which is typical of the psoriatic condition, secondly to ease the concomitant irritation, and finally to arrest the pathological condition in a relatively rapid manner, permitting the skin to return to a normal, healthy-looking state free from redness, scale, chapping and cracking. The period involved is usually two to four weeks.

EXAMPLE 9

Therapeutic Effect

The effect was first observed by chance in a factory environment wherein compositions of the present invention were in use for a non-medical purpose (see USSN 440 593). The tests of the present example were then organized ad hoc.

Eight volunteer adult sufferers from mild to moderate plaque-type psoriasis were selected for treatment during respective active episodes of the ailment. Five were males, three females; their ages ranged from 16 to 50. At least five of them had had prior professional diagnosis by a family physician. None was receiving intensive topical or systemic treatment at the time of the investigation. The body areas affected varied from one volunteer to another, but included the hands, forearms, elbows, face and, in one case, the scalp.

Each volunteer was provided with a quantity of the product of Example 8 containing, as active ingredient, HEPES in a proportion of 0.3% by weight, and was instructed to apply it to the affected areas of skin twice a day after washing. The instructions were carried out by all the volunteers.

Seven volunteers reported subjective improvement after periods varying from 7 to 14 days, and this was confirmed in all seven cases by lay observation, and in two cases by the family physician. One volunteer reported no noticeable change in symptoms for the better or the worse.

Four of the volunteers (2 male, 2 female) subsequently discontinued the treatment. All four reported a recurrence of symptoms after about 7 days. This was also confirmed by lay observation.

The remaining three volunteers have persisted with the treatment and have had no recurrence of symptoms with the last six months.

Several other workers in the same establishment, with no symptoms or history of inflammatory skin disease, applied the same product to their hands twice a day for an extended period (over two months), using it as a protective cream against accidental tissue adhesion by cyanoacrylate-type adhesives. None of these reported any deleterious effect, on the skin or otherwise. These results are preliminary and incomplete.

The same product was tested at the Biological Laboratories, Ballina, Co. Mayo, Ireland and found not to be a skin irritant.

Preliminary testing on animals is under way, in which a 1% Hydrocortisone cream is being used as a comparison, but the results are not yet to hand.

Application has been made, on the basis of these preliminary results, to the National Drugs Advisory Board of Ireland for approval for the setting up of systematic clinical tests.

Meanwhile the pharmacology of the ZASA's is under investigation in the Department of Clinical Medicine, Trinity College, Dublin.

While the number of sufferers treated to date with compositions of the invention is small, all of them have reported the relatively rapid improvement mentioned above. The face, hands, arms and elbows have all exhibited the kind of recovery described.

Although we do not wish to be bound by the terms of any theory, we suspect that pH control of the skin, coupled with the use of an aminosulfonic acid, is one factor in producing the effects we have seen. A major factor appears to be the recently discovered fact that the active ingredients of the compositions are effective in suppressing the functioning of neutrophils, a variety of white blood corpuscle. There is prior evidence to suggest that neutrophils, which are known to infiltrate into psoriatic lesions, are at least partly responsible for the damage to epidermal cell membranes which is characteristic of psoriasis. The evidence is summarised and amplified in two papers by M. M. Young and F. J. Bloomfield: (1) Influence of lithium and fluoride on degranulation from human neutrophils in vitro: *Inflammation,* Vol. 6, No. 3, 1982, pp. 257-267. (2) Enhanced release of inflammatory mediators from lithium-stimulated neutrophils in psoriasis: *British Journal of Dermatology* (1983) 108, Paper 607/6288.

The content of these papers is incorporated in the present description by reference. One of the authors (Bloomfield) is responsible for the discovery of neutrophil function suppression by ZASA's; the work is unpublished.

What I claim is:

1. A method of treating psoriasis which comprises applying to an affected area of skin a therapeutically effective amount of at least one skin-compatible zwitterionic aminosulfonic acid (one ZASA) having the formula

RNR'SO$_3$H wherein R represents tris-(hydroxymethyl)-methyl or the combination RN represents a radical selected from the group consisting of N-piperazinyl, N-morpholinyl, and N-[N'-(2-hydroxyethyl)]-piperazinyl; and R' is a C$_{2-4}$ straight or branched chain alkylene radical.

2. A method as recited in claim 1 which comprises applying a ZASA which has at least one pK$_a$ value at 20° C. in the range 6.0-8.3.

3. A method as recited in claim 1 wherein R' is selected from the group consisting of —CH$_2$—CH$_2$— and —CH$_2$—CH$_2$—CH$_2$—.

4. A method as recited in claim 1 wherein the ZASA is a member selected from the group consisting of
2-(N-Morpholinyl)-ethane sulfonic acid (MES),
2-[N-[N'-(2-Hydroxyethyl)]-piperazinyl]-ethane sulfonic acid (HEPES),
3-[N-[N'-(2-Hydroxyethyl)]-piperazinyl]-propane sulfonic acid (HEPPS),
2-[N-[tris-(Hydroxymethyl)]-methylamino]-ethane sulfonic acid,
2-(N-Piperazinyl)-ethane sulfonic acid,
2-(N-Piperazinyl)-propane sulfonic acid,
Piperazine-1,4-bis(2-ethane sulfonic acid) (PIPES) and N,N-bis-(2-Hydroxyethyl)-2-aminoethane sulfonic acid (BES).

5. A method as recited in claim 1 which comprises applying the ZASA at least once a day until the psoriatic condition has been relieved.

6. A method of treating psoriasis which comprises applying to an affected area of skin a therapeutically effective amount of at least one skin-compatible zwitterionic aminosulfonic acid (one ZASA) having the formula:

RNR'SO$_3$H wherein either R is a C$_{1-6}$ straight or branched chain aliphatic radical or the combination RN is a substituted or unsubstituted nitrogen-containing heterocyclic radical which may have one hetero-atom additional to the nitrogen atom that links said radical to R'; and R' is a C$_{2-4}$ straight or branched chain alkylene radical, said ZASA being non-toxic, non-carcinogenic and non-irritating.

7. A method as recited in claim 6 which comprises applying a ZASA which has at least one pK$_a$ value at 20° C. in the range 6.0-8.3.

8. A method as recited in claim 6 wherein R represents tris-(hydroxymethyl)-methyl.

9. A method as recited in claim 6 wherein RN represents a radical selected from the group consisting of N-piperazinyl, N-morpholinyl and N-[N'-(2-hydroxyethyl)]-piperazinyl.

10. A method as recited in claim 6 wherein R' is selected from the group consisting of —CH$_2$—CH$_2$— and —CH$_2$—CH$_2$—CH$_2$—.

11. A pharmaceutical composition for application to the human skin in the treatment of psoriasis comprising a therapeutically effective amount of at least one skin-compatible zwitterionic aminosulfonic acid (one ZASA) having the formula:

RNR'SO$_3$H wherein R represents tris-(hydroxymethyl)-methyl or the combination RN represents a radical selected from the group consisting of N-piperazinyl, N-morpholinyl, and N-[N'-2-(2-hydroxyethyl)]-piperazinyl; R' represents a C$_{2-4}$ straight or branched chain alkyene radical, and a pharmaceutically acceptable topical carrier or base, said pharmaceutical composition being in the form of a cream, solid, ointment or lotion.

12. A pharmaceutical composition as recited in claim 11 wherein the ZASA is a member selected from the group consisting of
2-(N-Morpholinyl)-ethane sulfonic acid (MES),
2-[N-[N'-(2-Hydroxyethyl)]-piperazinyl]-ethane sulfonic acid (HEPES),
3-[N-[N'-(2-Hydroxyethyl)]-piperazinyl]-propane sulfonic acid (HEPPS),
2-[N-[tris-(Hydroxymethyl)]-methylamino]-ethane sulfonic acid,
2-(N-Piperazinyl)-ethane sulfonic acid,
2-(N-Piperazinyl)-propane sulfonic acid,
Piperazine-1,4-bis(2-ethane sulfonic acid) (PIPES) and N,N-bis-(2-Hydroxyethyl)-2-aminoethane sulfonic acid (BES).

13. A pharmaceutical composition as recited in claim 11 wherein the ZASA has at least one pK$_a$ value at 20° C. in the range 6.0-8.3.

14. A pharmaceutical composition as recited in claim 11 wherein the proportion of ZASA is in the range 0.05 to 20% by weight of the composition.

15. A pharmaceutical composition as recited in claim 14 wherein the proportion is in the range 0.05 to 5%.

16. A pharmaceutical composition as recited in claim 15 wherein the proportion is in the range 0.1 to 1.0%.

17. A pharmaceutical composition for application to the human skin in the treatment of psoriasis as recited in claim 11, wherein R' is selected from the group consisting of —CH$_2$—CH$_2$— and —CH$_2$—CH$_2$—CH$_2$—.

18. A pharmaceutical composition for application to the human skin in the treatment of psoriasis comprising a therapeutically effective amount of at least one skin-compatible zwitterionic aminosulfonic acid (one ZASA) having the formula:

RNR'SO$_3$H wherein either R is a C$_{1-6}$ straight or branched chain aliphatic radical or the combination RN is a substituted or unsubstituted nitrogen-containing heterocyclic radical which may have one hetero-atom additional to the nitrogen atom that links said radical to R'; and R' is a C$_{2-4}$ straight or branched chain alkylene radical, said ZASA being non-toxic, non-carcinogenic, and non-irritating, and a pharmaceutically acceptable topical carrier or base, said pharmaceutical composition being in the form of a cream, solid, ointment or lotion.

* * * * *